United States Patent [19]
Schultz et al.

[11] Patent Number: 5,645,051
[45] Date of Patent: Jul. 8, 1997

[54] UNIT DOSE DRY POWDER INHALER

[75] Inventors: Robert K. Schultz, Poway; Robert F. Eisele, Laguna Niguel, both of Calif.

[73] Assignee: Dura Pharmaceuticals, Inc., San Diego, Calif.

[21] Appl. No.: 426,600

[22] Filed: Apr. 21, 1995

[51] Int. Cl.⁶ .................................................. A61M 15/00
[52] U.S. Cl. ................... 128/203.15; 128/203.21
[58] Field of Search ................... 128/203.15, 203.21; 604/58

[56] References Cited

U.S. PATENT DOCUMENTS

| | | | |
|---|---|---|---|
| 3,971,377 | 7/1976 | Damani | 128/203.15 |
| 4,452,239 | 6/1984 | Malem | 128/203.15 |
| 5,033,463 | 7/1991 | Cocozza | 128/203.15 |
| 5,327,883 | 7/1994 | Williams et al. | 128/203.15 |

FOREIGN PATENT DOCUMENTS

| | | | |
|---|---|---|---|
| 9007351 | 7/1990 | WIPO | 128/203.21 |
| 9204928 | 4/1992 | WIPO | 604/58 |

*Primary Examiner*—Aaron J. Lewis
*Attorney, Agent, or Firm*—Lyon & Lyon LLP

[57] ABSTRACT

A dry powder inhaler has a front section holding a unit dose cartridge over a mixing chamber. An impeller is rotatably mounted within the mixing chamber. A rear section of the inhaler includes a motor, a breath actuated switch, and pins for positioning the unit dose cartridge in the front section and driving a plunger through the unit dose cartridge, to deposit a powdered drug into the mixing chamber, as the front and rear sections are brought together. A filter wheel allows air to flow forward from the rear section into the mixing chamber, but substantially prevents stray drug powder from migrating rearwardly to the rear section. The front section is preferably disposable, while the rear section is advantageously reusable.

22 Claims, 3 Drawing Sheets

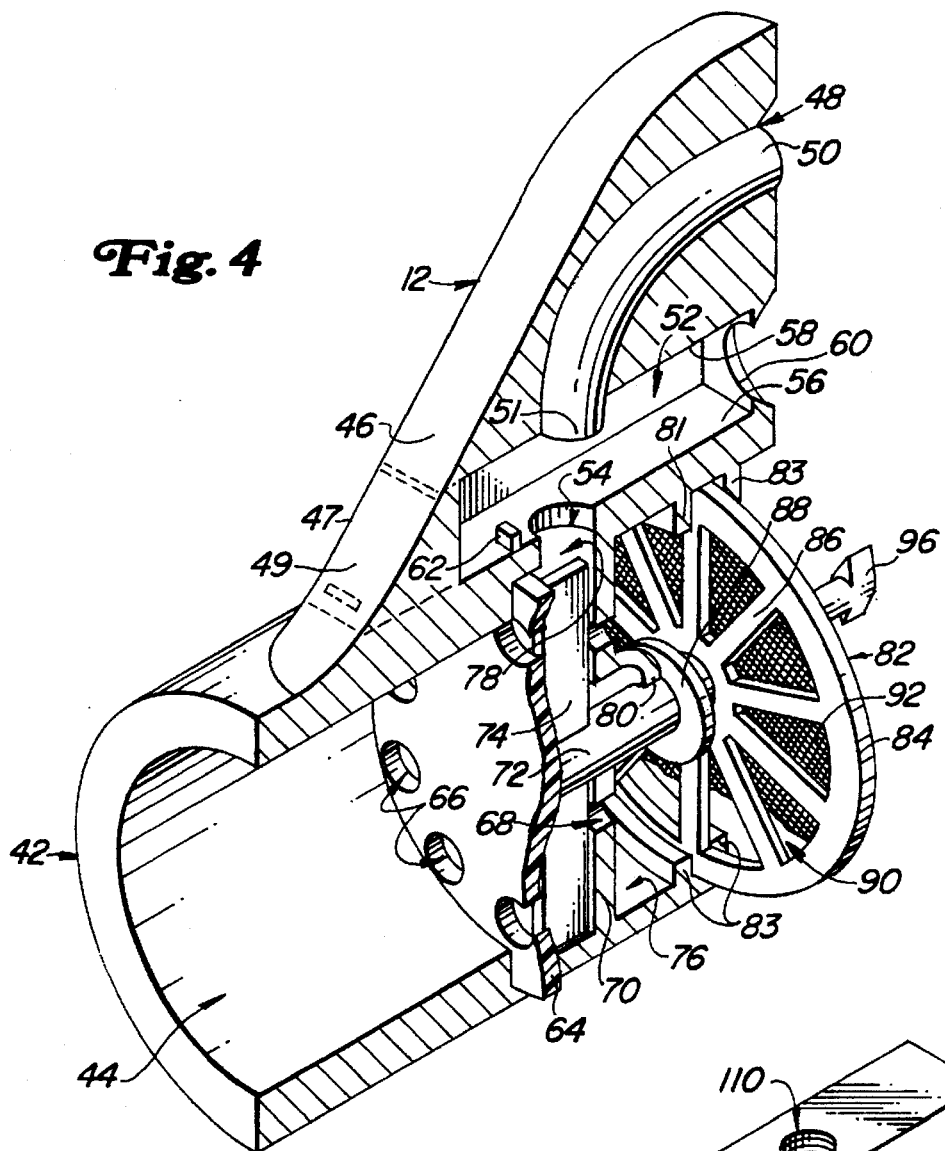
Fig. 4
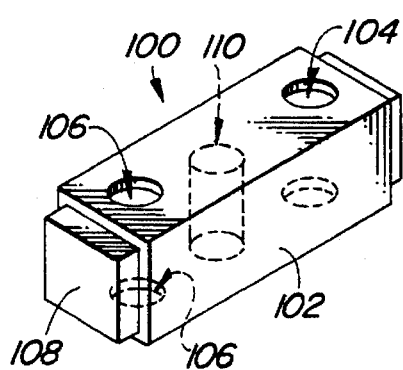
Fig. 5
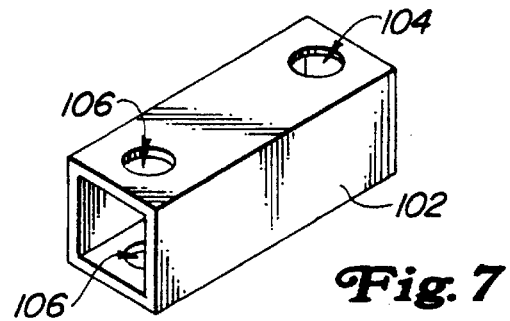
Fig. 6
Fig. 7

UNIT DOSE DRY POWDER INHALER

BACKGROUND OF THE INVENTION

1. Field of the Invention

The field of the invention is inhalers for dry powder inhalants or drugs.

2. Description of the Prior Art

Certain medicines may be taken in dry-powder form directly into the lungs by inhalation through the mouth or inspiration through the nose. This process allows the medicine to bypass the digestive system, and in some cases, allows smaller doses to be used to achieve the same desired results as orally ingested medicines. In other cases, it provides a delivery technique for medicines that display unacceptable side effects when taken by other methods.

Various known inhalers form mists or aerosols of liquid medicines or powdered medicines. However, these devices typically have various disadvantages, including lack of efficiency in delivering the medicine or drug; difficulties in loading and use; the need for repeated deep inhalation; non uniform dosing; caking of powdered medicines; and others.

While certain drugs, such as asthma drugs, may be taken several times daily, other drugs, including certain peptides or proteins are typically taken less frequently. Due to the delay in using these types of drugs, after they are removed from their packaging, providing a large number of doses within a single package is not desirable, as some doses may become unusable due to exposure to the environment. In addition, many drugs are susceptible to a short shelf life when removed from a foil storage pouch or other sealed container, even under nominal environmental conditions. These types of drugs must be used almost immediately after being exposed to the environment. Accordingly, there is a need for an inhaler for efficiently providing a prepackaged single dose of a powdered drug.

Ordinarily, with dry powder inhalers, it is difficult or impossible to insure that all powder of each dose is drawn out of the device. Consequently, especially with sticky or adhesive drugs, residual powder can tend to accumulate within the device. This accumulation of residual powder can adversely affect the operation of the device, result in inaccurate dose delivery, allow for bacterial growth within the device, and result in other adverse effects. Accordingly, there remains a need for a dry powder inhaler which overcomes the disadvantages of residual powder.

It is an object of the invention to provide such an improved dry powder inhaler.

SUMMARY OF THE INVENTION

To these ends a dry powder inhaler has a front or first section releasably attachable to a rear or second section. Preferably, the front section includes an impeller within a mixing chamber. A unit dose cartridge is advantageously positioned within a cartridge chamber over the mixing chamber. In a preferred embodiment, a plunger is positioned to push a unit dose of powdered drug out of the cartridge and into the mixing chamber. Preferably, the rear section includes a motor for spinning the impeller, and an actuator for driving the plunger through the cartridge, as the front section and rear section are attached to each other.

BRIEF DESCRIPTION OF THE DRAWINGS

Other objects and features of the present invention will become apparent from the following detailed description taken together with the accompanying drawings. The drawings, however, are provided for illustration purposes only and are not intended as a limitation on the scope of the invention.

In the drawings, wherein similar reference characters denote similar elements throughout the several views:

FIG. 4 is a perspective section view of the front section of the inhaler;

FIG. 5 is a perspective view of a unit dose cartridge;

FIG. 6 is a perspective view of the cylinder of the unit dose cartridge of FIG. 5;

FIG. 7 is a perspective view of the sleeve of the unit dose cartridge of FIG. 5.

DETAILED DESCRIPTION OF THE DRAWINGS

Figure 1:
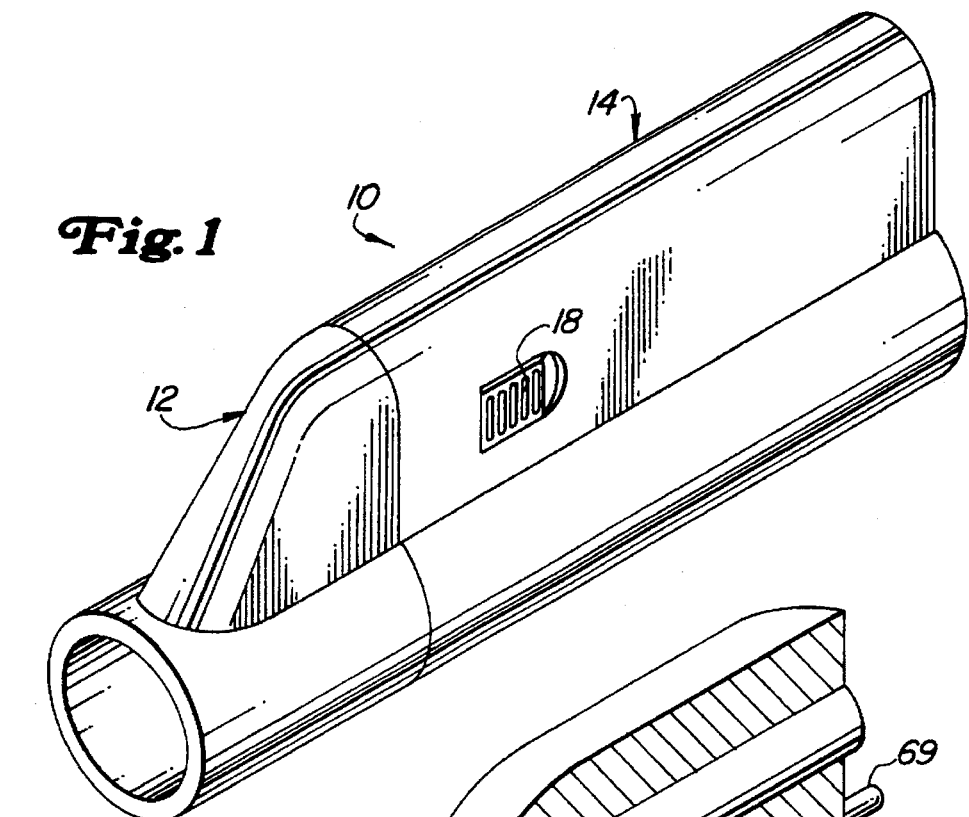
FIG. 1 is a perspective view of the inhaler of the invention.
Figure 3:
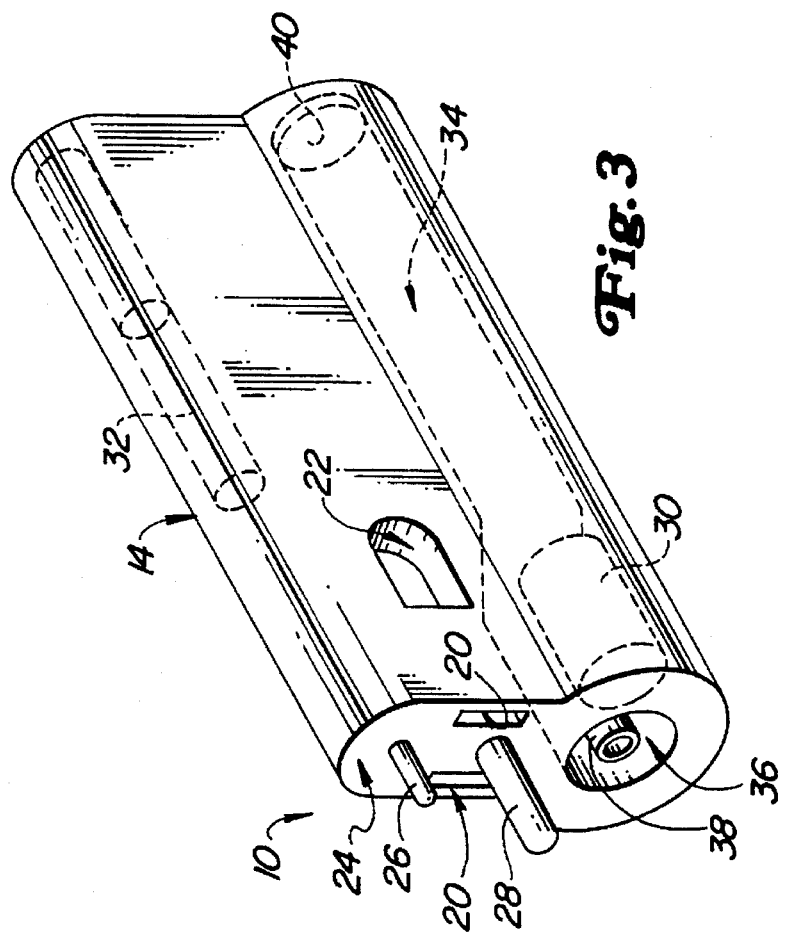
FIG. 3 is a perspective view of the rear section.
Figure 2:
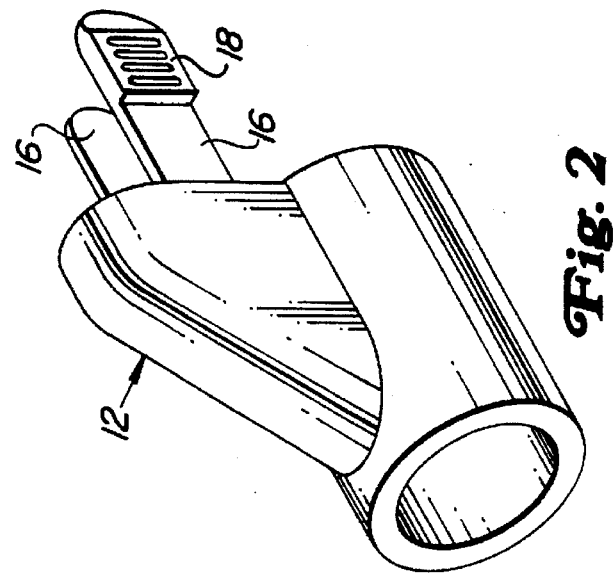
FIG. 2 is a perspective view of the front section.

Turning now in detail to the drawings, as shown in FIGS. 1, 2 and 3, a dry powder inhaler 10 has a front section 12 releasably attachable to a rear section 14, preferably using detent arms 16. Detents 18 on the arms 16 are extendable through arm slots 20 in the rear section 14. When fully engaged or attached together, with the flat front surface 24 of the rear section 14 abutting the flat rear surface of the front section 12, detents 18 on the arms 16 spring outwardly into recesses 22 on both sides of the rear section 14, thereby holding the front section 12 and the rear section 14 together.

Referring specifically to FIG. 3, a plunger pin 26 and a cylinder pin 28 extend forward from the front surface 24 of the rear section 14. Referring still to FIG. 3, a plenum 36 and an air channel 34 extending through the rear section 14 provide air flow to the front section. The rear section 14 includes an electric motor 30, batteries 32, a breath actuated switch 40, and air flow channels 34 as described in detail in Ser. No. 08/227,559, incorporated herein by reference.

Turning to FIG. 4, the front section 12 includes a cylinder mouthpiece 42 forming a front chamber 44. An upper section 46 on the front section 12 includes a flexible plunger 50 positioned within a plunger bore 48. A cartridge chamber 52 formed in the upper section 46 has a retaining lip 62 on the chamber floor 56. A rear wall 60 of the cartridge chamber 52 has an opening positioned to align with the cylinder pin 26 on the rear section 14. The rear end of the plunger 50 is nominally flush with the flat back surface of the front section 12, and the front end of the plunger 50 is correspondingly flush with the ceiling 58 of the cartridge chamber 52. A supply port 54 in the floor 56 of the cartridge chamber 52 is vertically aligned with the downwardly facing front end 51 of the plunger 50.

A disk-shaped mixing chamber 78 is formed in the front section 12 behind the front chamber 44 and below the cartridge chamber 52, between a front wall 64 and a rear wall 70. The front wall is fixed in place in the front section 12. Holes 66 extend through the front wall 64 at the perimeter, joining the mixing chamber 78 and the front chamber 44. An impeller 74 is supported within the mixing chamber 78 on a shaft 72 extending rearwardly through the rear wall 70 and a bearing surface 80, and then outwardly behind the flat rear surface of the front section 12. Openings 68 extend through the rear wall 70, adjacent the shaft 72.

A wheel 82 supported by the left and right halves of the front section housing, between front and rear rim wheel supports 81 and 83, has spokes 86 radiating out from the hub 88 to a rim 84, forming sector spaces 90 in between the spokes 86. The wheel hub 88 also provides a bearing surface. A filter material 92 is advantageously secured over the spokes 86 to prevent powder from flowing backwards through the sector spaces 90. Referring to FIGS. 2, 3 and 4, coupling hub 96 at the back end of the shaft 72 mates with a socket on a shaft 38 of the motor at the front of the rear section 14.

Turning to FIGS. 5, 6 and 7, a unit dose cartridge 100 has an outer sleeve 102 having front through holes 106 and rear blind hole 104. A cylinder 108 within the sleeve 102 has a centrally located powder bore 110. The cylinder advantageously fits within the sleeve 102 with sufficiently close tolerances to prevent significant migration of the powdered drug out of the powder bore 110.

In use, in a controlled environment (such as a factory or lab) the cylinder 108 is positioned within the sleeve 102 with the powder bore 110 aligned with the rear hole 104. Powder is then loaded into the powder bore 110, through the rear hole 104 in the sleeve 102. The bottom surface of the sleeve 102 has no hole corresponding or aligned with hole 104 on the top surface of the sleeve 102. Accordingly, the powder cannot significantly fall or migrate out of the powder bore 110.

After the powder bore 110 is filled, the cylinder 108 is moved forwardly to the position shown in FIG. 5 with the filled powder bore 110 now centrally located. The open ends of the powder bore 110 are generally closed off by the top and bottom surfaces of the sleeve 102. The unit dose cartridge 100 is then positioned within the cartridge chamber 52. The retaining lip 62 on the floor 56 of the cartridge chamber 52, and the rear wall 60 of the cartridge chamber, position the cartridge 100 so that the downwardly facing front end 51 of the plunger 50 aligns with the front hole 106 of the sleeve 102 of the cartridge 100. The front hole 106 in the bottom surface of the sleeve 102 correspondingly aligns with the supply port 54. The retaining lip 62 is high enough to catch and hold the sleeve 102, but without interfering with forward sliding movement of the cylinder 108.

The front section 12 is advantageously formed with a left side (as shown in FIG. 4) and a corresponding right side which is attached to the left side after the cartridge 100 is installed. The left and right sides are attached with snapping fasteners, screws, adhesives, or other well known attachment techniques.

With the filled cartridge 100 or an equivalent drug carrier installed and the left and right sides of the front section 12 assembled, the front section is then preferably sealed within a package or container, such as a foil envelope, within a controlled environment. The drug powder within the cartridge 100 can accordingly be isolated from harmful environmental conditions, e.g., humidity, dust, light, etc.

The entire front section is advantageously made of low cost materials, so that it may serve as a disposable single dose unit.

Referring to FIGS. 1, 2 and 3, when the inhaler 10 is ready for use by a patient, the front section 12 is removed from its container or package. The detents 18 are aligned with the arm slots 20 and the front and rear sections brought together. As this movement occurs, the cylinder pin 28 moves through the opening in the rear wall 60 of the cartridge chamber 52 and pushes the cylinder forward. The length of the cylinder pin 28 is selected, along with the dimensions of the cartridge 100, to cause the powder bore 110 to align with the front end of the plunger 51, and the supply port 54, when the front section 12 and rear section 14 are fully mated together. As the front and rear sections are slid together, and after the cylinder 108 has been moved forward by the cylinder pin 28, the plunger pin 26 engages and pushes against the plunger 50, driving the plunger into and through the powder bore 110. The drug powder contained in the powder bore 110 is accordingly fully driven out of the powder bore 110, through the supply port 54, and into the mixing chamber 78. Other mechanical equivalents can of course also be used to drive the drug into the mixing chamber.

The plunger 50 is advantageously sufficiently flexible, with low sliding friction, so that it can move through the plunger bore 48, with only low to moderate force. The length of the plunger pin 26 is substantially less than the length of the cylinder pin 28, and is selected so that as the front and rear sections are brought together, the plunger 50 does not begin to move until the powder bore 110 is appropriately positioned over the supply port 54. In addition, the length of the plunger pin 26 is sufficient to drive the front end 51 of the plunger 50 entirely through the cartridge 100 and supply port 54, to thereby substantially seal off the supply port 54 after the drug powder has been pushed into the mixing chamber 78, when the front and rear sections are fully mated together. The elastic nature of the plunger 50 can provide a squeegee action to scrape powder from the walls of the powder bore 110.

As the front and rear sections are brought together, the detents 18 on the detent arms 16 slide through the arm slots 20, and spring outwardly, with the detents 18 projecting into the recesses 22, on either side of the rear section 14, when the front and rear section are fully mated. The detents 18 then hold the front and rear sections together during use of the inhaler.

Simultaneously, the coupling hub 96 on the shaft 72 extending behind the front section 12 moves into and engages with a corresponding coupling on the shaft of the electric motor 30 within the rear section 14. The shaft and motor coupling hubs are self-aligning.

With the front and rear sections mated together, the inhaler 10 is ready for use. The mouthpiece 42 is placed in the mouth. As the patient inhales, air is drawn through the air channel 34, through the plenum 36 and into the front section 12. The breath actuated switch 40, detecting the air movement, switches on the motor 30, powered by the batteries 32. The motor spins the shaft 72, and impeller 74 in the bearing surface of the wheel and hub, which are fixed in the housing. The impeller 74 fits closely between the front wall 64, rear wall 70 and circumferential wall 76, thoroughly mixing and deagglomerizing the drug powder and air, as described in detail in Ser. No. 08/227,559. Air flowing forward from the plenum 36 passes through the filter material 92 covering the sector spaces 90 in the spinning wheel 82. Openings 68 in the rear wall 70 adjacent to the shaft 72 allow air to flow into the mixing chamber 78. The air/drug mixture formed within the mixing chamber 78 flows through the holes 66 in the front wall 64, into the front chamber 44 and from there into the patient's mouth, throat and lungs, with the characteristics described in Ser. No. 08/227,559. The flat mating surfaces of the front and rear sections provide a sufficient seal to prevent significant leakage, for the (negative) pressures and durations involved.

After the inhalation of the unit dose from the powder bore is complete, the front section 12 is separated from the rear section 14 by depressing the detents 18 inwardly and pulling the front and rear sections apart. The front section is then preferably discarded, while the rear section is reusable. The filter material 92 on the wheel 82 allows air to flow forwardly through the front section 12, but does not allow stray powder to migrate rearwardly into the rear section 14, thereby avoiding any substantial residual drug accumulation on the rear section 14. As the front section 12 is advantageously discarded, the disadvantages of accumulation of residual powder within the inhaler are avoided.

When the rear section 14 is not in use, a cover is preferably placed over the front surface 24, to prevent contaminants from entering the plenum 36. The inhaler 10 accordingly provides for effective delivery of the powdered drug, and is especially useful for delivery of unit doses via disposable front section 12.

Figure 8:
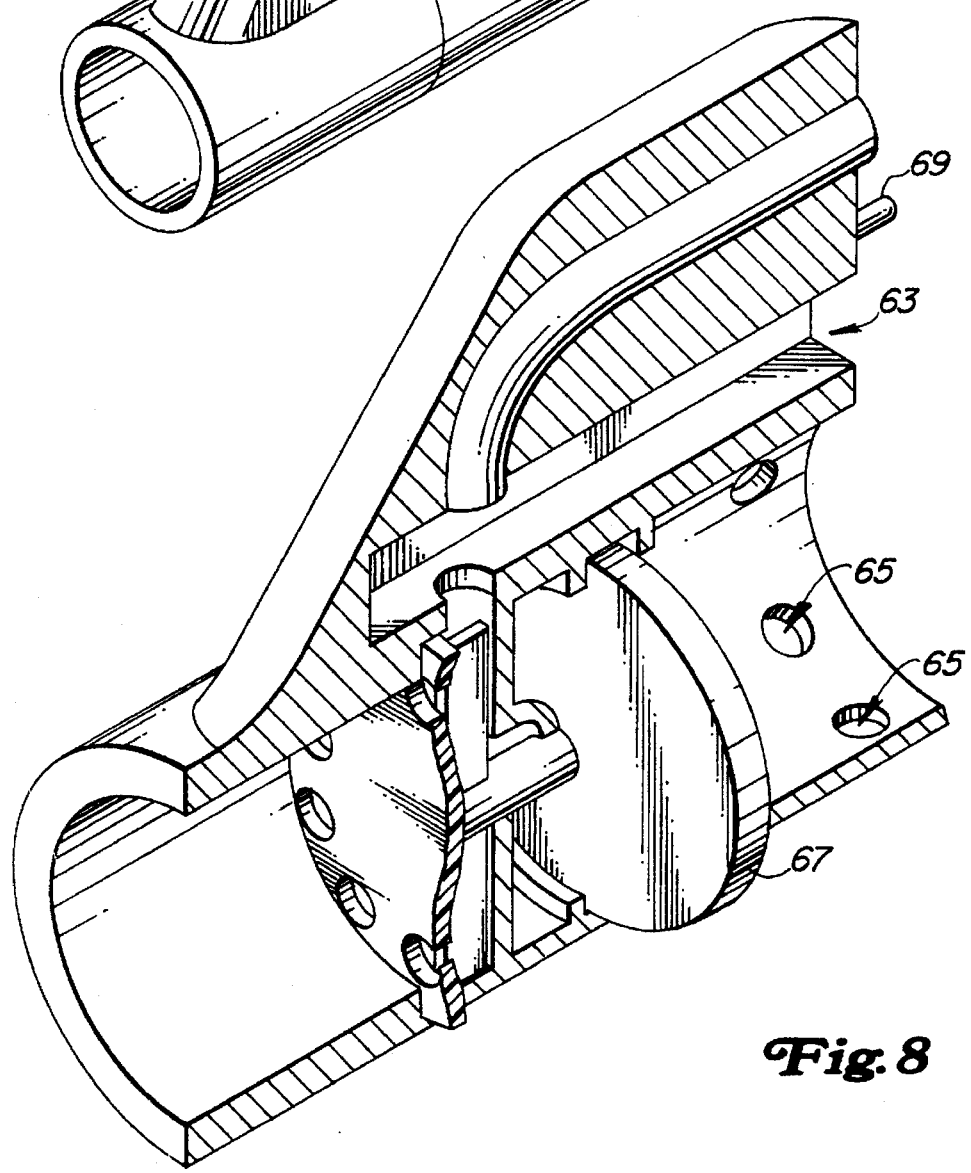
FIG. 8 is a perspective view of an alternative embodiment.

In an alternative embodiment, the cartridge chamber 52 can be modified to allow for multiple uses with certain drugs, in a semi-disposable manner. Specifically, the opening 63 in the rear chamber wall 60 (FIG. 8) is enlarged so that the cartridge 100 or an equivalent can be used and then pulled back out of the cartridge chamber, allowing for reuse of the front section with another cartridge. In an alternate modification, the cartridge chamber 52 can be extended through to the front surface 47 of the upper section 46, as shown in phantom line in FIG. 4. A door covering the front opening of the cartridge chamber can be opened to remove the used cartridge from the front 47 of the front section 12, after lifting it over the retaining lip 62. As shown in FIG. 8, in another preferred embodiment, a breath actuated switch 67 is positioned in the front section 12, generally replacing the wheel 82. Inlet holes 65 behind the switch 67 allow air to be drawn into the front section, instead of flowing in from the rear section. An electrical contact 69 and wiring links the switch 69 in the front section to the motor and circuitry in the rear section.

Thus, while the invention has been described with reference to a particular embodiment, those skilled in the art will be able to make various modifications without departing from the spirit and scope of the invention.

We claim:

1. A dry powder inhaler comprising:
    a front section including:
        a mixing chamber;
        an impeller rotatably mounted in the mixing chamber;
        a powdered drug carrier containing a powdered drug; and
        a supply port extending between the drug carrier and the mixing chamber; and
    a rear section attachable to the front section and including a motor for spinning the impeller; and
    a plunger in the front section aligned with the powdered drug and the supply port, when the front section is attached to the rear section.

2. The dry powder inhaler of claim 1 further comprising a holding chamber for holding the powdered drug carrier.

3. The dry powder inhaler of claim 2 further comprising a drive pin extending out of the rear section and extendible into the holding chamber.

4. The dry powder inhaler of claim 1 further comprising a plunger pin extending out of the rear section and engageable to the plunger.

5. A dry powder inhaler comprising:
    a front section including, a mixing chamber, a unit dose cartridge containing a powdered drug, and a passageway leading from the unit dose cartridge to the mixing chamber;
    a rear section attachable to the front section;
    means for moving the powdered drug from the cartridge into the mixing chamber when the front section is attached to the rear section.

6. The dry powder inhaler of claim 5 wherein the means for moving comprises a plunger pin on the rear section for opening the unit dose cartridge when the front section and the rear section are brought together.

7. The dry powder inhaler of claim 6 wherein the means for moving further comprises a flexible plunger in the front section, the flexible plunger having a front end aligned with the drug contained in the unit dose cartridge, and having a rear end aligned with the plunger pin.

8. The dry powder inhaler of claim 5 wherein the means for moving comprises a plunger pin on the rear section for opening the unit dose cartridge when the front section and the rear section are brought together.

9. The dry powder inhaler of claim 8 wherein the means for moving further comprises a flexible plunger in the front section, the flexible plunger having a front end aligned with the drug contained in the unit dose cartridge, and having a rear end aligned with the plunger pin.

10. The dry powder inhaler of claim 5 wherein the unit dose cartridge comprises an outer sleeve having front through holes and a rear blind hole, and a cylinder within the sleeve having a powder bore.

11. The dry powder inhaler of claim 5 wherein the unit dose cartridge and the front section are disposable and are sealed within a package.

12. The dry powder inhaler of claim 5 wherein the front and rear sections have flat mating surfaces.

13. A dry powder inhaler comprising:
    a front section including a mixing chamber, a powdered drug carrier containing a powdered drug, and a passageway leading from the powdered drug carrier to the mixing chamber;
    a rear section attachable to the front section flow and including a battery, a breath actuated switch and an air flow channel; and
    means for moving the powdered drug from the powered drug carrier into the mixing chamber when the front section is attached to the rear section.

14. The dry powder inhaler of claim 13 wherein the means for moving comprises a plunger pin on the rear section for opening the unit dose cartridge when the front section and the rear section are brought together.

15. The dry powder inhaler of claim 14 wherein the means for moving further comprises a flexible plunger in the front section, the flexible plunger having a front end aligned with the drug contained in the unit dose cartridge, and having a rear end aligned with the plunger pin.

16. The dry powder inhaler of claim 13 further comprising an impeller in the mixing chamber and a shaft on the impeller extending into the rear section to connect to the motor.

17. The dry powder inhaler of claim 13 further comprising a filter material between the mixing chamber in the front section and the motor in the rear section.

18. A dry powder inhaler comprising:
    a from section including a mixing chamber, a powdered drug carrier containing a powdered drug, and a passageway leading from the powdered drug carrier to the mixing chamber;
    a rear section attachable to the front section;
    a motor in the rear section;
    an impeller in the mixing chamber and a shaft on the impeller extending into the rear section to connect to the motor; and
    means for moving the powdered drug from the powdered drug carrier into the mixing chamber when the front section is attached to the rear section.

19. The dry powder inhaler of claim 18 further comprising a battery, a breath actuated switch and an air flow channel in the rear section.

20. The dry powder inhaler of claim 19 further comprising a filter material between the mixing chamber in the front section and the motor in the rear section.

21. The dry powder inhaler of claim 18 wherein the drug carrier comprises a unit dose cartridge.

22. The dry powder inhaler of claim 21 wherein the unit dose cartridge and the front section are disposable and are sealed within a package.

* * * * *